(12) United States Patent
Rögl et al.

(10) Patent No.: US 7,687,668 B2
(45) Date of Patent: Mar. 30, 2010

(54) PROCESS FOR PREPARING 4,4′ DIFLUOROBENZOPHENONE

(75) Inventors: Harald Rögl, Wallern an der Trattnach (AT); Markus Ungerank, Perg (AT)

(73) Assignee: Evonik Fibres GmbH, Lenzing (AT)

( * ) Notice: Subject to any disclaimer, the term of this patent is extended or adjusted under 35 U.S.C. 154(b) by 0 days.

(21) Appl. No.: 11/989,790

(22) PCT Filed: Jul. 27, 2006

(86) PCT No.: PCT/EP2006/007426

§ 371 (c)(1),
(2), (4) Date: Aug. 5, 2008

(87) PCT Pub. No.: WO2007/014692

PCT Pub. Date: Feb. 8, 2007

(65) Prior Publication Data

US 2009/0177014 A1 Jul. 9, 2009

(30) Foreign Application Priority Data

Aug. 4, 2005 (DE) .................. 10 2005 037 337

(51) Int. Cl.
*C07C 45/30* (2006.01)
(52) U.S. Cl. .................. 568/312; 568/316; 568/322

(58) Field of Classification Search .................. 568/312, 568/316, 332
See application file for complete search history.

(56) References Cited

U.S. PATENT DOCUMENTS 4,792,635 A   12/1988   Marhold et al.

FOREIGN PATENT DOCUMENTS

EP   0 004 710   10/1979

OTHER PUBLICATIONS

Wang, S. et al., Synthesis of bis-(4-N, N-dimethylaminophenyl)-methane in Jingxi Huagong Zhongjianti, 2004,ISSN:1009-9212, 34(4), 26-27, 2004.
J. Lichtenberger, R. Thermet: "Preparation de quelques derives flures en serie aromatique" Bulletin de la Societe Chimique de France., 1951, pp. 318-325, XP002405822 Frsociete Francaise de Chimie. Paris. p. 321-p. 322.

*Primary Examiner*—Sikarl A Witherspoon
(74) *Attorney, Agent, or Firm*—Hamilton, Brook, Smith & Reynolds, P.C.

(57) ABSTRACT

Process for preparing 4,4′-difluorobenzophenone, characterized in that, in a first step, fluorobenzene is reacted with formaldehyde under catalysis by organic sulphonic acids to give difluorodiphenylmethane, the product obtained is isolated, and, in a second step, oxidized with nitric acid to give 4,4′-difluorobenzophenone. 4,4′-Difluorobenzophenone (4,4′-DFBP) is the central starting material for the preparation of aromatic polyether ketones.

5 Claims, No Drawings

PROCESS FOR PREPARING 4,4' DIFLUOROBENZOPHENONE

RELATED APPLICATIONS

This application is the U.S. National Stage of International Application No. PCT/EP2006/007426, filed Jul. 27, 2006, published in German, and claims priority under 35 U.S.C. §365 to German Application No. 10 2005 037 337.2, filed Aug. 04, 2005.

The present invention relates to processes for preparing 4,4'-difluorobenzophenone and its isomers. 4,4'-Difluorobenzophenone (4,4'-DFBP) is the central starting material for preparing aromatic polyether ketones. These are high-performance polymers with constantly growing annual production volumes, so that the volume of 4,4-DFBP produced worldwide annually is also included in the growth. The most important polyether ketones are the polyether ether ketones (PEEK) and polyether ketones (PEK). These feature melting points of above 330° C. and high chemicals resistance. Small amounts are used to produce medicaments and agrochemicals.

At the present time, 4,4'-DFBP is obtained almost exclusively in the following 2-stage synthesis according to U.S. Pat. No. 2,606,183 (1952) and U.S. Pat. No. 2,705,730 (1995), both Head et al.: first, 4,4'-diaminodiphenylmethane (MDA for methylene dianiline) is diazotized with $NaNO_2$ in HF solution, and the fluoride ion is introduced into the aromatic with $HBF_4$ according to Balz-Schiemann with $N_2$ evolution (see Beyer, Walter, Lehrbuch der organischen Chemie [Textbook of organic chemistry], Hirzel, 24th edition, 2004, page 626, and Balz, Schiemann, Berichte, vol. 60, p. 1186 (1927)). According to this, the 4,4'-difluorodiphenylmethane (DFDPM) formed, after purification, is oxidized with $HNO_3$.

According to EP-A-0004710, Staniland et al. (1979) and U.S. Pat. No. 2,563,796 (Shenk et al.), it is also possible to decompose the diazonium fluoride dissolved in hydrofluoric acid directly by heating.

A second route to the synthesis of benzophenones is the Friedel-Crafts acylation, which is effected either directly from fluorobenzene and phosgene according to U.S. Pat. No. 4,618,762 (Desbois (1986)) in hydrofluoric acid and with boron trifluoride as the catalyst, or, according to U.S. Pat. No. 4,814,508 (Gors et al. (1989)), from fluorobenzene and 4-fluorobenzoyl chloride with aluminum chloride and lithium chloride as the catalyst.

A third means of synthesis is nucleophilic substitution of the aromatic (SNAr). This either exchanges a nitro group (U.S. Pat. No. 6,274,770, Clarc et al., 2001) for a fluorine atom with tetramethylammonium fluoride as the phase transfer catalyst (PTC), or a halide (JP-A-57169441) for a fluorine atom with potassium fluoride at elevated temperature (from 150° C. to 200° C.). A further means of obtaining 4,4'-difluorobenzophenone is described in JP-A-61221146 (Fukuoka et al. 1986). Fluorobenzene is reacted with carbon monoxide and oxygen in the autoclave with the aid of a noble metal catalyst.

DE-A-698 15 082 describes the synthesis from 4,4'-dinitrodiphenylmethane. The oxidation is effected with air in dimethylacetamide; according to this, the nucleophilic substitution of the aromatic takes place with the aid of tetramethylammonium fluoride as the PTC. The yield is about 70%. The reaction is carried out with 60 mg of starting substance in 10 ml of solvent, meaning that this is not an industrially utilizable process.

U.S. Pat. No. 4,978,798 describes a multistage, complicated process in which trihalomethylbenzene is first reacted with a halobenzene which contains at least two chloride substituents in the presence of a Lewis acid. The bisphenyldihalomethane formed is then treated with water to form a halobenzophenone. Chloride substituents are then exchanged for fluoride in two steps.

The search for different syntheses for preparing difluorobenzophenone, which has proceeded over several decades, indicates that none of them is without serious disadvantages.

In the variant via Friedel-Crafts acylation, a particular disadvantage is the high demand for catalysts and their disposal. In the Balz-Schiemann reaction, a particular problem is the hydrofluoric acid solvent and the workup of the tetrafluoroboric acid. In addition, large amounts of inorganic salts are obtained here too.

Nucleophilic substitution to obtain difluorobenzophenone has to date not gained any industrial significance. 4,4'-Dichlorobenzophenone is not cheap as a starting substance and actually just shifts the problem to the preparation of a doubly para-substituted benzophenone. Released nitro groups from the 4,4'-dinitrobenzophenone form nitrates which can quite possibly initiate side reactions at the temperatures used and economically viable concentrations.

In view of the prior art discussed above, it is an object of the invention to provide a further simple process for synthesizing 4,4'-difluorobenzophenone.

This object is achieved by coupling fluorobenzene with formaldehyde under acid catalysis to form an isomer mixture of 2,4'- and 4,4'-DFDPM which is subsequently oxidized to the corresponding benzophenone. The benzophenone isomers are separated by recrystallization.

This process offers the following advantages:
1. Both in the coupling and in the oxidation, apart from by-products, only water and no other by-product occurring in a stoichiometric amount is formed.
2. Both reactions can proceed at standard pressure and temperatures between 0° C. and 100° C., which significantly reduces the apparatus complexity.
3. The acidic catalyst can be regenerated by heating under reduced pressure.

The invention provides a process for preparing 4,4'-difluorobenzophenone, wherein, in a first step, fluorobenzene is reacted with formaldehyde with catalysis by organic sulfonic acids to give difluorodiphenylmethane, and the product obtained is isolated and, in a second step, oxidized with nitric acid to give 4,4'-difluorobenzophenone.

After the first step, a mixture of about 95% difluorodiphenylmethane isomers (DFDPM) and 5% more highly condensed products is obtained.

The difluorodiphenylmethane formed consists of about 77% 4,4'-DFDPM and 23% 2,4'-DFDPM. This isomer mixture can be separated from the by-products by vacuum distillation, but not separated into its isomers.

After the first step, the organic sulfonic acid is removed and worked up.

Excess fluorobenzene is likewise removed from DFDPM before the vacuum distillation.

Fluorobenzene is a good starting substance for fluorine-containing organic compounds, since it is prepared on the industrial scale and is relatively inexpensive.

Fluorobenzene is used in excess for the first step of the reaction, and it is simultaneously the solvent.

The more dilute the solution is, the smaller the amount of more highly condensed by-products, measured by DFDPM, are formed.

The molar ratio of fluorobenzene to formaldehyde is between 5:1 and 30:1, preferably between 8:1 and 12:1.

Formaldehyde is preferably used in the form of trioxane or in the form of paraformaldehyde. However, it is also possible to introduce dry, gaseous formaldehyde.

Organic sulfonic acids suitable as catalysts are, for example, methanesulfonic acid, ethanesulfonic acid, trifluoromethanesulfonic acid, benzenesulfonic acid, m-benzenedisulfonic acid, benzene-1,3-5-trisulfonic acid, 2,4-dinitrobenzenesulfonic acid, p-toluenesulfonic acid and fluorobenzenesulfonic acid (FBSA) or naphthalenedisulfonic acid.

FBSA has the advantage over methanesulfonic acid that it is soluble in fluorobenzene and brings about a distinctly more rapid reaction even at temperatures below 45° C. without shifting the isomer ratio of 4,4'-DFDPM to 2,4'-DFDPM unfavorably, as is usual at relatively high temperatures.

One advantage of FBSA in comparison to p-toluenesulfonic acid is that, after the first reaction step, no cleavage products of the catalyst have to be removed from the system.

The use of FBSA as the catalyst is preferred. FBSA is generally present as an isomer mixture of 4-fluorobenzenesulfonic acid and 2-fluorobenzenesulfonic acid.

The reaction temperature in the first step is generally from −15° C. to 70° C., preferably from −15° C. to 45° C., more preferably from 0° C. to 25° C.

In the second step, the DFDPM isomer mixture is oxidized with nitric acid at a temperature of from 50° C. to 130° C., preferably from 65° C. to 100° C., and the 4,4'-DFBP formed is isolated in isomerically pure form by recrystallization. The isomer separation can be effected by recrystallization from a mixture of acetic acid and water, which is both economically and ecologically advantageous, since no additional solvent is required aside from the acetic acid.

In a further optional embodiment of the process according to the invention, the nitrous gases formed in the oxidation with nitric acid in the second step are oxidized with molecular oxygen and converted to nitric acid with water, in analogy to the Ostwald process. In this reaction, either pure oxygen or air can be used.

The process according to the invention will be illustrated by way of example below:

1.1 Reaction of Fluorobenzene with Formaldehyde

Anhydrous FBSA is dissolved in fluorobenzene and paraformaldehyde is added in powder form, and the mixture is stirred for several hours with removal of the heat of reaction. The following reaction takes place:

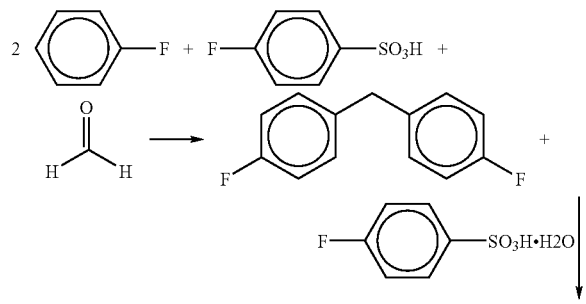

Fluorobenzene is used in excess and is simultaneously the solvent.

The molar ratio of fluorobenzene to formaldehyde is between 5:1 and 30:1, preferably between 8:1 and 12:1. The FBSA is an isomer mixture of 4-fluorobenzenesulfonic acid and 2-fluorobenzenesulfonic acid.

The water eliminated in the reaction forms an insoluble monohydrate with the FBSA.

This begins to crystallize out even after a few minutes of reaction time. FBSA therefore has to be used in an equimolar amount to formaldehyde, better with a slight excess.

The colder the solution is, the more advantageous is the ratio of 4,4'-DFDPM to 2,4'-DFDPM. 2,2'-DFDPM is not formed.

The temperature is between −15° C. and +70° C., preferably between 0° C. and 30° C. The first time of the reaction is advantageously carried out at low temperature; toward the end, the temperature can be increased for faster completion of the reaction.

1.2 Removal and Workup of the FBSA

At the end of the reaction, a small amount of water (approx. 1 g per 4 g of FBSA used) is added.

The crystals liquefy. The acidic phase settles at the bottom. It is removed and washed once again with pure fluorobenzene.

The FBSA can be worked up in two ways:
heat up to 140° C. under reduced pressure, which almost fully removes the water or
heat briefly up to 120° C. under reduced pressure, extract the solution which still contains water with fluorobenzene and heat the fraction insoluble in fluorobenzene again.

FBSA is formed industrially by sulfonating fluorobenzene with concentrated sulfuric acid.

Sulfonation is a reversible reaction. Therefore, as the aqueous FBSA is heated, a little fluorobenzene, which evaporates immediately, and sulfuric acid are formed. The sulfuric acid has to be removed, since it, in the anhydrous state, carbonizes the paraformaldehyde by water removal. The higher the temperature, the more marked this back reaction is. Fluorobenzene eliminated in this reaction need not be removed from the plant.

This is the essential advantage of FBSA in comparison to p-toluenesulfonic acid. Toluene eliminated has to be removed from the system rigorously, since it would otherwise react with paraformaldehyde and fluorobenzene to give 4-methyl-4'-fluorodiphenylmethane.

In the case of gentle removal of the water, the formation of toluene is so low that the resulting losses of yield are low. The use of p-toluenesulfonic acid is then preferable owing to the easy availability of FBSA.

1.3 Removal of the Fluorobenzene and Vacuum Distillation of DFDPM

The organic phase of the last step is washed at room temperature first with a little water and then with a sodium carbonate solution, and the majority of fluorobenzene is drawn off at standard pressure and then the rest under reduced pressure of approx. 25 mbar at approx. 90° C. Any crystals formed by residues of the sodium carbonate solution are filtered off. The filtrate consists of DFDPM isomers and more highly condensed products.

The former distill over at absolute pressure 25 mbar in the range between 130° C. and 140° C. without separation of the isomers. At these temperatures, none of the more highly condensed secondary constituents distill over yet.

When the temperature is increased up to 200° C. in the bottom of the distillation apparatus, these secondary constituents, though, are also found increasingly in the distillate. This small fraction has to be double-distilled.

The bottoms consist of the secondary constituents and also about 25%-35% DFDPM.

1.4 Oxidation with Nitric Acid

The DFDPM isomer mixture is preferably oxidized with HNO$_3$ at temperatures of from 65° C. to 100° C.

When a mixture of 102 g (0.50 mol) of DFDPM with 500 ml of 65% HNO$_3$ (2.5 mol) is heated to 75° C. with stirring for 15 hours, the oxidation proceeds quantitatively with formation of nitrous gases. In the course of cooling, the organic phase, when the temperature goes below 50° C., solidifies to a waxy mass which is held together by small crystals of 4,4'-DFBP. This mass is separated from the aqueous phase and recrystallized.

In a further preferred embodiment of the process according to the invention, firstly the high demand for nitric acid and secondly the complicated offgas cleaning can be avoided by downstream connection of an absorber unit. This unit converts the nitrous gases formed by the oxidation with nitric acid back to nitric acid with oxygen as the oxidizing agent.

This variant of the process according to the invention is described by way of example below:

A three-neck flask with thermometer, stirrer and heater is utilized as the oxidation reactor.

A second, equally large three-neck flask with stirrer, cooler and connection to an oxygen-filled gas balloon functions as the absorber. The gas spaces of the two flasks are connected to one another and, with the gas balloon, form a closed system. In addition, two pumps are installed. The first pumps nitric acid from the reaction flask into the absorber, the other nitric acid from the absorber into the reaction flask.

DFDPM in the reaction flask is blanketed with about one third of the volume of 25% nitric acid and stirred gently. At this low concentration, the nitric acid floats at the top. The same amount of nitric acid with the same concentration enters the absorber. At the start, the entire gas space of both flasks is flooded with pure oxygen. The reaction flask is heated to approx. 65° C., and to approx. 75° C. after 3 hours. In the absorber cooled to approx. 25° C., the mixture is stirred vigorously in order to increase the surface area between gas space and liquid by spraying droplets. The nitrous gases formed in the reaction flask pass into the absorber. Under cold conditions, they are oxidized by the oxygen and dissolved in the liquid to form nitric acid. This is entirely analogous to the preparation of nitric acid by the Ostwald process. The enriched nitric acid is pumped into the reaction flask and depleted acid is pumped therefrom into the absorber with the same delivery output.

In this reaction system, oxygen is consumed and, viewed overall, no other gas is obtained. Oxygen is sucked out of the attached balloon until the reaction stops. After the end of the oxidation, all of the nitric acid is available again for a next batch, apart from minimal losses as a result of nitration of DFDPM.

The nitric acid is merely diluted by the water formed in the oxidation.

In this way, it acts only as a catalyst of the oxidation, which is carried out de facto with molecular oxygen.

In the course of cooling, the organic phase solidifies to a waxy mass.

1.5 Recrystallization 4,4'-DFDPM can be obtained in virtually any purity by repeated recrystallization with a mixture of glacial acetic acid and water (9:1) as the solvent from the wavy mass obtained after the oxidation. To this end, the oxidation product is mixed with one and a half times the amount of solvent and heated. At about 80° C.-90° C., the solution becomes homogeneous. In the course of cooling, a crystal slurry forms, from which a crude product of about 95% purity can be filtered off by suction filtering. A purity of at least 99.5% can be achieved by recrystallizing a total of three times, always in the same amount of solvent.

The crystals removed by suction filtering are dried at 90° C. under reduced pressure.

The mother liquor after the first recrystallization step is concentrated by evaporation under reduced pressure to recover the solvent.

What is claimed is:

1. A process for preparing 4,4'-difluorobenzophenone, comprising the steps of:
    a) reacting fluorobenzene with formaldehyde, in the presence of an organic sulfonic acid catalyst, to yield difluorodiphenylmethane;
    b) isolating the difluorodiphenylmethane obtained in step a);
    c) oxidizing the isolated product obtained in step b) with nitric acid to yield 4,4'-difluorobenzophenone.

2. The process as claimed in claim 1, wherein the reaction in step a) is carried out in fluorobenzene as a solvent and the organic sulfonic acid catalyst is fluorobenzenesulfonic acid 3. The process as claimed in claim 1, wherein the reaction in the step a) is carried out at a temperature between −15° C. and 70° C.

4. The process as claimed in claim 1, further comprising step d) converting nitrous gases resulting from the oxidation of difluorodiphenylmethane to nitric acid with an oxidizing agent.

5. The process as claimed in claim 4, wherein the oxidizing agent is oxygen.

* * * * *